United States Patent
Hardy et al.

[11] Patent Number: 5,299,449
[45] Date of Patent: Apr. 5, 1994

[54] LIQUID FLOW REACTOR AND METHOD OF USING

[75] Inventors: Dennis R. Hardy, Alexandria, Va.; Erna J. Beal, Fort Washington; Jack C. Burnett, Oxon Hill, both of Md.

[73] Assignee: The United States of America as represented by the Secretary of the Navy, Washington, D.C.

[21] Appl. No.: 875,955

[22] Filed: Apr. 30, 1992

[51] Int. Cl.$^5$ ................................................ G01N 5/00
[52] U.S. Cl. ................................. 73/61.62; 73/61.72
[58] Field of Search ................ 73/53.01, 61.41, 61.62, 73/61.63, 61.71, 61.72

[56] References Cited

U.S. PATENT DOCUMENTS

| | | | |
|---|---|---|---|
| 3,059,467 | 10/1962 | Megverian et al. | 73/61.62 |
| 3,063,289 | 11/1962 | Moul | 73/61.72 |
| 3,108,468 | 10/1963 | Mickel | 73/61.62 |
| 3,438,248 | 4/1969 | Taylor et al. | 73/61.62 |
| 3,670,561 | 6/1972 | Hundere | 73/61.62 |
| 5,036,699 | 8/1991 | Fikentscher et al. | 73/61.62 |
| 5,101,658 | 4/1992 | Wilson, III et al. | 73/61.62 |

Primary Examiner—Hezron E. Williams
Assistant Examiner—Michael Brock
Attorney, Agent, or Firm—Thomas E. McDonnell; Barry A. Edelberg

[57] ABSTRACT

The tendency of liquid hydrocarbon-based fuels, such as kerosene, diesel fuel, and jet fuel toward the formation of fuel-insoluble solids during thermal stress in an aircraft fuel system is assessed by an accelerated test method comprising passing a predetermined quantity of a sample of fuel through a heated test section maintained at a predetermined temperature, at a predetermined fuel flow rate. A metal test strip, weighed before the test, is clamped in the heated test section during the test. It is weighed again after the test and the weight of solids buildup during the test is determined. It is related directly to the tendency of the fuel to form fuel-insoluble solids during thermal stress. A filter is weighed before the test. It is then connected to the outlet of the test section, and liquid fuel leaving the test section during the test is passed through it. The filter is then weighed a second time and the weight increase of the filter due to its capture of fuel-insoluble solids is calculated. It also is directly related to the tendency of the fuel to form fuel-insoluble solids during thermal stress.

9 Claims, 2 Drawing Sheets

LIQUID FLOW REACTOR AND METHOD OF USING

BACKGROUND OF THE INVENTION

1. Field of the Invention

This invention relates to a method for assessing the tendency of hydrocarbon-based liquid fuels to form insoluble products during thermal stress encountered in aircraft fuel systems. More specifically, it relates to an accelerated method for assessing such insoluble product formation which avoids subjective human judgment, such as the color of a test specimen, and relies on an objective, gravimetric measurement.

2. Description of the Prior Art

Hydrocarbon-based fuels such as kerosene, diesel fuel, and jet fuel tend to form fuel-insoluble solid products during thermal stress, defined as exposure to elevated temperature for short or prolonged periods of time. Liquid fuels are normally exposed to such thermal stress in aircraft fuel systems. Fuel-insoluble solids may clog fuel filters and fuel atomizing nozzles in engines, coat heat exchanger surfaces, and obstruct close-tolerance fuel control mechanisms, thereby causing operating problems.

The formation of fuel-insoluble solids in hydrocarbon-based liquid fuels is a function of the presence in the fuel of certain chemical components which at present have not been identified. Empirical test methods are therefore needed for assessing the tendency of any given fuel to form fuel-insoluble solids during thermal stress in an aircraft fuel system. As a practical matter, such tests must be completed within about 24 hours. There is a need therefore for an accelerated test method for assessing the formation of fuel-insoluble solids in a fuel which yields results within a few hours.

U.S. Pat. No. 3,647,404 describes a thermally stable turbine or jet fuel composition comprising a mineral oil distillate and a low concentration of an additive inhibiting the formation of fuel-insoluble solids in turbine or jet fuels.

SUMMARY OF THE INVENTION

The object of the present invention is to provide an apparatus and a method for assessing the tendency of liquid hydrocarbon-based fuels, including diesel fuel, jet fuel, and kerosene, to form fuel insoluble solids during thermal stress encountered in aircraft fuel systems. A further objective is to provide apparatus and a method for such tests which yield quantitative results within a few hours, as opposed to testing procedures which sometimes take much longer, which depend on highly subjective human judgment, and which do not provide precise quantitative measurements.

The objectives of the present invention are achieved by introduction of a standardized quantity of hydrocarbon-based liquid fuel, at a standardized fuel flow rate, to a standardized heated test section in which has been placed a standardized metal test strip on which fuel-insoluble solids build up during the test run, the gain in weight of the test strip due to insoluble solids buildup being directly related to the tendency of the fuel to form such insoluble solids during thermal stress encountered in an aircraft fuel system.

A further measure of the tendency of the fuel toward formation of insoluble solids during thermal stress is provided by a filter through which fuel having passed through the heated test section flows. The gain in weight of the filter due to the capture of fuel-insoluble solids entrained from the heated test section during the test run provides a second quantitative measure of the tendency of the fuel toward formation of insoluble solids during thermal stress. Alternatively, the effluent fuel may be collected and filtered subsequently.

DESCRIPTION OF THE PREFERRED EMBODIMENT

Figure 1:
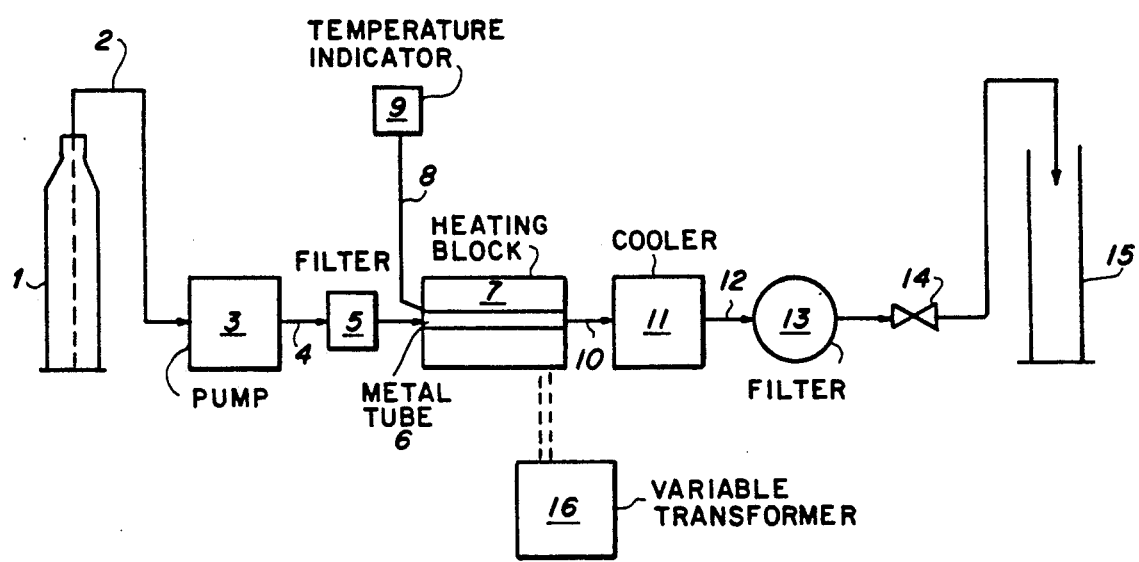
FIG. 1 shows a schematic flowsheet of a testing system in accordance with the present invention.

With reference to FIG. 1, a distillate fuel sample is placed in a supply bottle 1, from which it passes via a tube 2 into a pump 3. From the pump 3, the fuel flows via a tube 4 and a filter 5 into a piece of metal tubing 6 which is located in a heating block 7 having electrical resistance windings, whose temperature is measured by a thermocouple 8 and indicated by a temperature indicator 9.

Figure 2A:
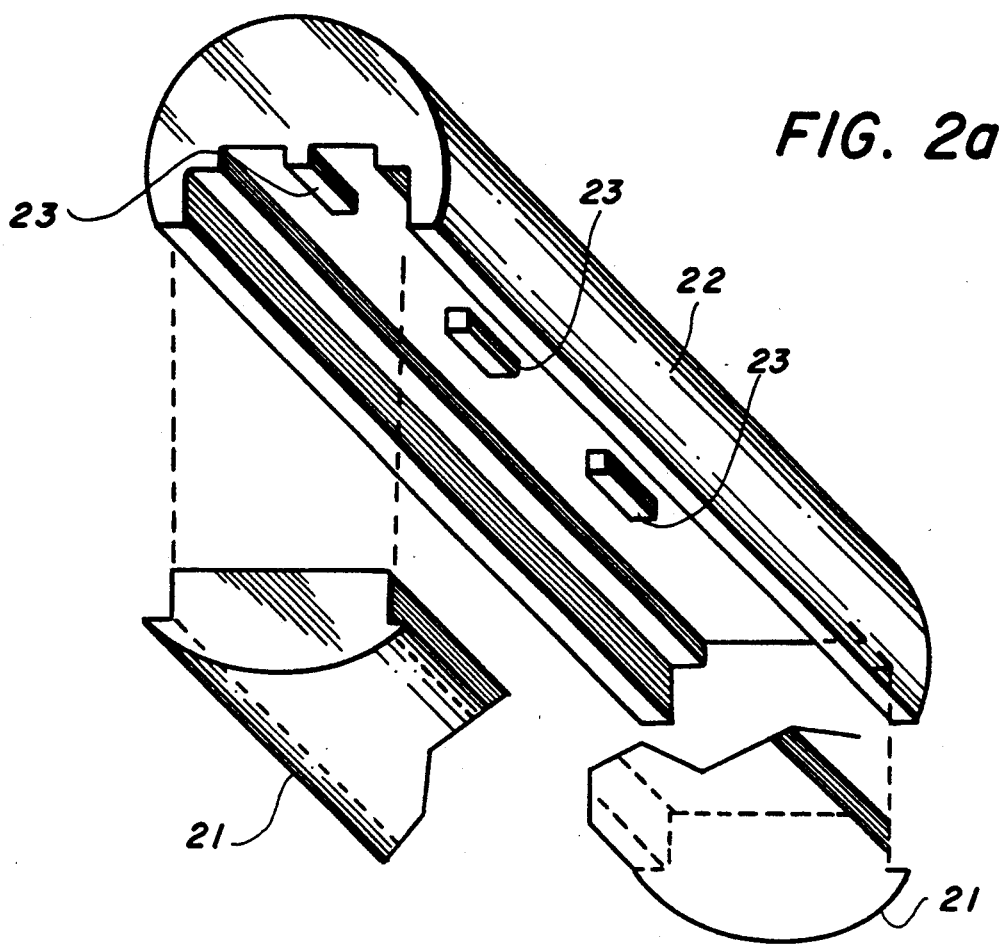
FIGS. 2a and 2b show isometric views of the components of an insert in the test apparatus of this invention.
Figure 2B:
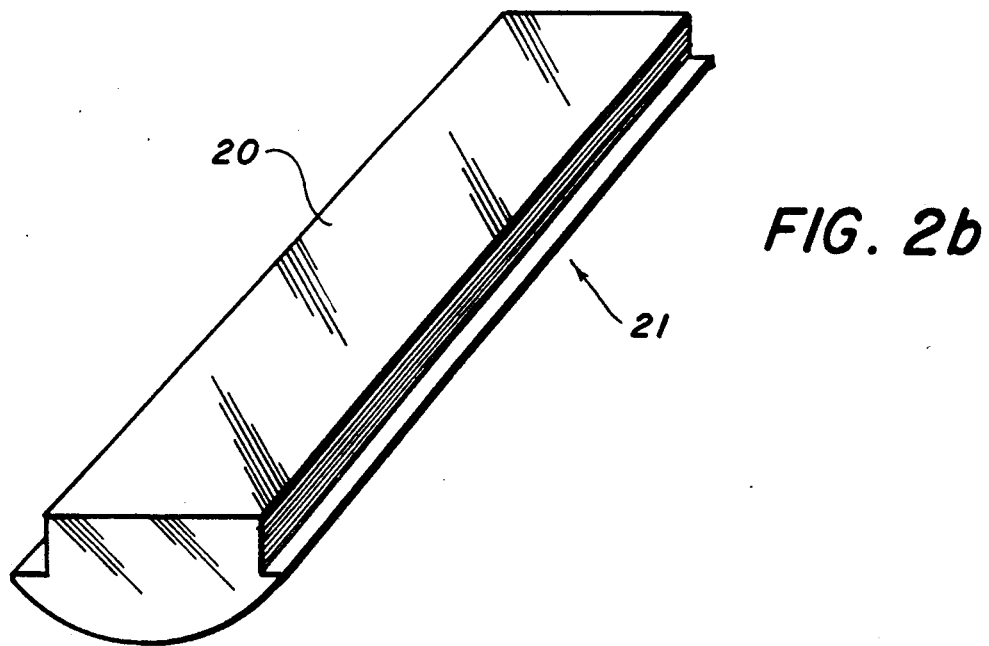

Inside the tubing 6, there is placed an insert as illustrated in FIGS. 2a and 2b. Onto a flat surface 20 on the lower part of the insert, 21, there is placed a thin test strip of metal foil, e.g. stainless steel, (not shown) of known weight, and the upper part of the insert, 22, is lowered onto the lower part of the insert, clamping the metal test strip between the flat part of the lower part of the insert 21 and projections 23 on the upper part of the insert, 22. The assembled upper and lower parts of the insert, with the metal test strip clamped therebetween, is inserted into the tubing 6, the fit between the perimeter of the assembled insert and the inside of the tubing 6 being snug. The tubing 6, the insert, and the heating block 7, constitute the test section as defined herein.

The outlet end of tubing 6 connects to a tube 10. During testing, fuel flows through the insert in tube 6, coming in contact with the metal test strip clamped between the upper and lower parts of the insert, and exits through tube 10. From here, it flows through a cooler 11, through a tube 12 to a filter 13 of known weight and a throttle valve 14 for maintaining pressure inside the test apparatus. The fuel exits from the throttle valve and drops into a receiving vessel 15. Alternatively, the filter 13 may be omitted and the fuel from vessel 15 may be subsequently filtered and the filtercake weighed.

The heating block 7 is electrically heated, temperature control being provided by a variable transformer (VARIAC ®) 16, or other thermostatic heat controller.

The tendency of the fuel being tested toward the formation of insoluble solids is assessed after a given amount of fuel has been passed through the test apparatus at a predetermined temperature and a predetermined flow rate, by shutting down the apparatus, disconnecting the tubing 6, removing the insert and the metal test strip, and weighing it. The weight increase of the metal test strip over its original weight is a measure of the buildup of insoluble solids on the foil strip during the test. The filter 13 is also weighed. The weight increase of the filter over its original weight is yet another measure of the buildup of insoluble solids during the test.

On the basis of the gravimetric measurements of insoluble solids buildup during the test on a fuel sample, it can be determined whether a given fuel meets specifications as to insoluble solids formation or whether insoluble solids formation is excessive, necessitating chemical fuel pretreatment, such as catalytic hydrotreatment, to avoid excessive formation of fuel-insoluble solids during thermal stress in aircraft fuel systems.

In the preferred embodiment of this invention, the tubing 6 is about 100 mm long, its outside diameter is 12.7 mm (0.500″), and its inside diameter 10.7 mm (0.42″). The lower and upper parts of the insert, 21 and 22, when assembled, have an outer diameter of about 10.7 mm, thus fitting snugly into the tubing 6 so that, during the test, no fuel bypasses around the periphery of the insert, but all fuel flows through the central portion of the insert with the metal test strip. The length of the insert is about 100 mm. The width of the flat portion of the lower insert, 20, is about 7 mm. The metal test strip is about 80 mm long, 7 mm wide, and about 25 microns thick. Its weight ranges from 105 to 110 mg. Type 302 austenitic stainless steel is preferred, but other metals and metal alloys may be substituted since certain metals are known distinctly to affect the formation of insoluble solids formation. Foils are preferred as the test strip. Most preferably, the metal of the test strip is chosen to simulate the fuel system in which the fuel will be used.

A liquid fuel flow rate of about 3.0 ml/min is preferred during the test. The quantity of fuel tested during any test run is preferably about 450 ml. The heating block temperature during the test preferably is about 260 degrees C.

EXAMPLE 2

A sample of fuel having a high tendency toward insoluble solids formation, tested at 3.0 ml/minute flow rate at 260 degrees C., showed a solids buildup on the metal test strip of 0.038 mg. The filter gained 6.73 mg in weight during the test. The total amount of insoluble solids collected thus is 6.768 mg.

EXAMPLE 2

A sample of fuel having a low tendency toward insoluble solids formation, tested under the same conditions as above, showed a solids buildup of 0.007 mg on the metal test strip and a gain in weight of the filter of 0.47 mg, for a total solids collected of 0.477 mg. The second sample is seen to have formed a very significantly lower amount of solids during the standardized test as described than the first sample.

It is apparent that considerable variations in dimensions and operating conditions of this type of apparatus are possible without departing from the spirit of the invention. Thus, the length of the tubing constituting the test section may range from 50 to 1000 mm, the outside diameter may range from 6 to 50 mm, the inside diameter from 5 to 45 mm, the fuel flow rate from 1 to 1000 ml/min, the fuel quantity per test run from 50 ml to 5 liters, and the heating block temperature from about 200 to about 350 degrees C. The residence time of the liquid fuel in the heated test section during the test may range from 1 second to 30 minutes. The metal test strip may be from 3 to 30 mm wide, from 25 to 250 mm long, from 10 to 50 microns thick, and may be made of any ferrous alloy, nonferrous alloy, or elemental metal, chrome-nickel austenitic steel, specifically Type 302 stainless steel, being preferred.

Further details concerning the present invention may be found in "Development of a Jet Fuel Thermal Stability Flow Device Which Employs Direct Gravimetric Analysis of Both Surface and Fuel Insoluble Deposits'—Presented at ASTM meeting, June 1991: To be published in ASTM Special Technical Publication No. 1138, Aviation Fuel: Thermal Stability Requirements, published by ASTM, Philadelphia, Pa., 1992, wholly incorporated by reference herein; "Results and Evaluation of a Jet Fuel Thermal Stability Flow Device Which Employs Direct Gravimetric Analysis of Both Surface and Fuel Insoluble Deposits" and "The Effect of Temperature on Jet Fuel Thermal Stability Using a Flow Device Which Employs Direct Gravimetric Analysis of Both Surface and Fuel Insoluble Deposits", both of which were presented at the 4th International Conference on Stability and Handling of Liquid Fuels, November 1991, and published in the Proceedings of that conference, by CRC Publishers, April 1992, both of which are wholly incorporated by reference herein.

The physical arrangement described for clamping a metal test strip in the test apparatus is one of many possible methods of holding test strips which will be apparent to those skilled in the art and which are within the spirit of this invention.

What is claimed is:

1. Apparatus for the rapid determination of the tendency of liquid hydrocarbon-based fuels to form fuel-insoluble solids, comprising:
    a test section comprising a metal tube having included therein an insert for holding a metal test strip, said insert having upper and lower parts, whichسandwich said metal test strip therebetween, and a heating means to heat said test section;
    means of introducing a sample of liquid distillate fuel to said test section;
    a metal test strip; and
    means for removing said liquid distillate fuel from said heated test section after making contact with said metal test strip.

2. Apparatus in accordance with claim 1, in which said means for introducing said sample of liquid distillate fuel to said test section is a pump connected on its suction side to a sample reservoir, and on its discharge side to an inlet of said test section.

3. Apparatus in accordance with claim 1, in which said heating means of said test section is comprised of resistance heating wires connected to a source of electric energy.

4. Apparatus in accordance with claim 1, in which said test strip is made of austenitic stainless steel.

5. Apparatus in accordance with claim 1, in which said means for removing said liquid distillate fuel from said heated test section is a tube connecting an outlet of said test section to a cooler and a receiving vessel.

6. Apparatus in accordance with claim 5, further including a filter for removing solids from said liquid distillate fuel, connected between said cooler and said receiving vessel.

7. The apparatus in accordance with claim 1, wherein said metal test strip is a thin metal foil.

8. A test method of determining the tendency of liquid hydrocarbon-based fuels to form fuel-insoluble solids comprising:
    weighing a metal test strip a first time;
    flowing a sample of liquid hydrocarbon fuel through a heated test section, said heating test section comprising an outer tube having a cylindrical insert snugly fit therein, said cylindrical insert including an upper part, a lower part and a central portion therebetween, said metal test strip being clamped in said central portion by said upper part and said lower part;

controlling fuel pressure in said heated test section by throttling the flow of fuel downstream of said heated test section, thus maintaining said fuel pressure;

stopping the flow of said liquid hydrocarbon fuel and removing said metal test strip from said test section;

weighing said metal test strip a second time; and calculating the weight of solids buildup on said metal test strip while said sample of liquid hydrocarbon fuel is flowing through said heated test section based upon weight difference of said metal test strip between said first and second weighings.

9. The method of claim 8, wherein said outer tube of said test section has an inner diameter of from 5 to 45 mm, said fuel is controlled to flow at a rate of from 1 to 1000 ml/min, and from 50 ml to 5 liters of said fuel resides in said heated test section for from 1 second to 30 minutes.

* * * * *